United States Patent [19]
Cummings, Jr.

[11] Patent Number: 5,301,105
[45] Date of Patent: Apr. 5, 1994

[54] ALL CARE HEALTH MANAGEMENT SYSTEM

[75] Inventor: Desmond D. Cummings, Jr., 2309 Orchard Dr., Apopka, Fla. 32715

[73] Assignee: Desmond D. Cummings

[21] Appl. No.: 683,032

[22] Filed: Apr. 8, 1991

[51] Int. Cl.$^5$ ............................................. G06F 7/00
[52] U.S. Cl. ................................... 364/401; 364/406; 364/408
[58] Field of Search ..................... 364/401, 406, 408

[56] References Cited

U.S. PATENT DOCUMENTS

| | | | |
|---|---|---|---|
| 3,697,693 | 10/1972 | Deschenes et al. | |
| 4,290,114 | 9/1981 | Sinay | 364/900 |
| 4,491,725 | 1/1985 | Pritchard | 235/375 |
| 4,648,037 | 3/1987 | Valentino | 364/408 |
| 4,797,543 | 1/1989 | Watanabe | 235/492 |
| 4,858,121 | 8/1989 | Barber et al. | 364/406 |
| 4,916,611 | 4/1990 | Doyle, Jr. et al. | 364/401 |
| 5,018,067 | 5/1991 | Mohlenbrock et al. | 364/413.02 |

OTHER PUBLICATIONS

Excerpt from Mesa Petroleum, Company. Mesa Solution Magazine entitled "Corporate America At Risk" Pages four through eleven.

*Primary Examiner*—Roy N. Envall, Jr.
*Assistant Examiner*—Gita D. Shingala

[57] ABSTRACT

A fully integrated and comprehensive health care system that includes the integrated interconnection and interaction of the patient, health care provider, bank or other financial institution, insurance company, utilization reviewer and employer so as to include within a single system each of the essential participants to provide patients with complete and comprehensive pretreatment, treatment and post-treatment health care and predetermined financial support therefor.

102 Claims, 9 Drawing Sheets

ALL CARE HEALTH MANAGEMENT SYSTEM

This invention relates to managed health care systems and more particularly to managed health care systems which address health enhancement life styles, illness prevention, case management, illness treatment and post treatment monitoring and/or review; and which integrate physicians, medical care facilities, patients, insurance companies and/or other health care payers, employers and banks and/or other financial institutions.

BACKGROUND OF THE INVENTION

A variety of medical payment systems have heretofore been proposed illustrative of which are those disclosed in U.S. Pat. No. 4,491,725 granted to Lawrence E. Pritchard on Jan. 1, 1985 and in U.S. Pat. No. 4,858,121 which was granted to William B. Barber et al. on Aug. 15, 1989.

According to the proposals of the prior art, systems have been proposed which include one or more magnetic and manual entry data entry terminals at the health care provider facilities, various verification and authentication routines, data storage which includes lists of insurance companies or other payers together with lists of medical procedures for which such payers are obligated to make payments, schedules of permissible fees for such procedures and selected data related specifically to each covered patient.

Other proposals of the prior art have included examination of participants to determine their physical condition, identification of existing physical profiles and encouragement of changes in life styles, where indicated, to enhance the physical condition of the participant and to lessen the likelihood of the development of disease.

However, such systems have not heretofore featured the total health care function, for they have not integrated important elements of total health care such as comprehensive preventive health measures, the review of the necessity for implementing selected procedures including changes in life styles, the obtaining of second opinions, (i.e., utilization review/case management) and other functions contemplated by total health management such as ancillary services. Neither have they included integration of the active participation by a patient's employer or inclusion of a patients' own available cash balances. Accordingly, since these missing functions are important ingredients to extend proposals of the prior art to fully comprehensive medical care, there has continued to be a need for a system which provides full integration of each of the aforementioned activities.

BRIEF SUMMARY OF THE INVENTION

The preferred embodiment of the present invention includes the integrated interconnection and interaction of the patient, health care provider, bank or other financial institution, utilization reviewer/case manager and employer so as to include within a single system each of the essential elements to provide patients with complete and comprehensive health care and payment therefor. it additionally contemplates, as an optional feature, the complete integration of all aspects of "wellness", that is, of the optimization of health-inducing diet and life style factors in combination with the aforementioned enhanced integrated diagnosis, treatment and post-treatment of illnesses when they do occur, and quality monitoring and enhancement systems including patterns of treatment protocols and diagnostic smart systems that will serve as aids in treatment planning and diagnostic test selection.

OBJECTS AND FEATURES

It is one general object of this invention to provide a fully integrated health optimization system.

It is another object of this invention to improve medical treatment systems.

It is another object of the invention to provide a wholly integrated health care management system.

It is still another object of the invention to provide an integrated health care management system including interactive participation with patients' employers and banks.

It is still another object of the invention to include in an integrated health care management system the interactive participation of a utilization review for recommended medical procedures.

It is yet another object of the invention to integrate preventive medical programs with treatment programs, thereby to encompass the full gamut of health wellness.

Accordingly, in accordance with one feature of the invention, all of the elements of health enhancement are integrated, including customized planning, prevention, treatment and rehabilitation, thus facilitating health wellness management, improving efficiency and reducing costs.

In accordance with the foregoing feature, integrated service is provided, thus reducing time, direct cost, and indirect cost often incurred through duplication of tests, excessive paperwork and inappropriate utilization, thus enhancing the ability of the system to provide quality health care through case management and physician interaction via smart systems.

In accordance with yet another feature of the invention, the planning and preventive aspects of health wellness includes the provision of customized recommendations for health-enhancing practices and for the periodic monitoring of participants' physical conditions, diets and life styles so as to identify and address incipient health problems and provide corrective measures before health problems develop.

In accordance with another feature of the invention, provision is made for health management of selected groups of participants as well as for individuals.

In accordance with still another feature of the invention, provision is made for integrated operation in both in-patient and out-patient modes of treatment.

In accordance with yet another feature of the invention, provision for integrated operation is provided for inclusion of ancillary services such as those provided by pharmacists, dentists, optometrists, audiologists and related laboratories.

In accordance with still another feature of the invention, the system is made flexible so that it is compatible with procedures required for implementing workmen's compensation processing.

In accordance with yet another feature of the invention, provision is made for optional precertification of patients and procedures, thus enhancing health care efficiency and reducing overhead costs.

In accordance with another feature of the invention, provision is made for patient discharge planning and monitoring.

In accordance with another feature of the invention, interactive communication links are provided with an integrated utilization review whereby for predetermined selected medical procedures proposed for implementation there is performed a utilization review which may optionally include second opinions.

In accordance with still another feature of the invention, the aforementioned utilization review which can be customized according to predetermined criteria, thus improving diagnosis, treatment and cost effectiveness.

In accordance with yet another feature of the invention, provision is made for both concurrent and retrospective utilization reviews.

In accordance with yet another feature of the invention, quality control is provided through interpretation of the aforementioned utilization reviews.

In accordance with still another feature of the invention, provision is made for on-line test results, digitized imaging, and projection on high resolution CRT screens in physician's offices.

In accordance with another feature of the invention, there is included within the system a link between the claims processing and the patients' employer, thereby providing important information transfer on a real time basis and the capability for employer override.

In accordance with yet another feature of the invention, banks or other repositories of funds are integrated into the system so as to provide automated transfer of funds to accounts of physicians and other health care providers.

In accordance with still another feature of the invention, provision is made for implementation of discretionary patient cost-sharing and/or supplementation to supplement approved fees and to obtain a selected medical treatment with a sharing of costs by the insurance company or other payer for the basic amount and with a supplement by the patient for any remaining residue.

In accordance with one other feature of the invention, the system is responsive to the utilization of either conventional credit-type cards or with "smart" cards that are specially dedicated for use with the system.

The foregoing and other objects and features of the invention will be apparent from the following detailed description, by way of a description of a preferred embodiment, with reference to the drawings.

DESCRIPTION OF A PREFERRED EMBODIMENT

Figure 1:
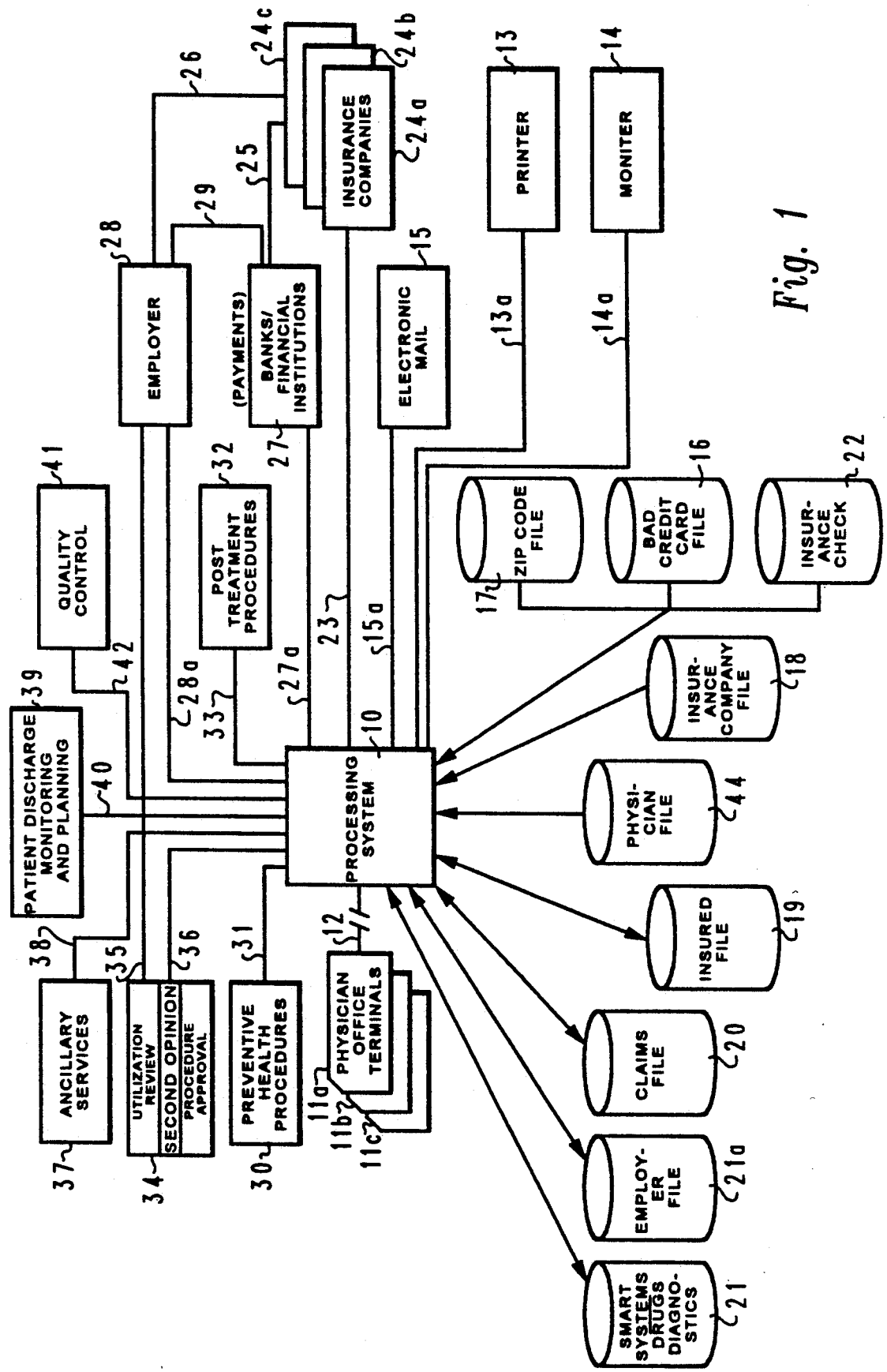
FIG. 1 is a block diagram depicting principal functional elements of the improved Wellness Health Management System.

Now turning to the drawing, and more particularly FIG. 1 thereof, it will be observed that it depicts the principal components of a preferred system in accordance with the principles of the invention. Depicted there are processing system 10 which is interconnected with one or more physician office terminals 11a-11c by conventional communication paths 12. Terminals 11a-11c may be any of a variety of conventional data input terminals (e.g., such as that shown in FIG. 2 and described below) that provide for pre-recorded card and/or manual data entry input. Also included are conventional printer 13 (linked to Processing System 10 via link 13a) and monitor 14 (linked to Processing System 10 via link 14a), monitor 14 preferably having a high resolution CRT screen positioned in a location within the physician's office so as to facilitate observation and review. This monitor may be of the type normally available with current state of the art Personal Computers.

The inclusion of an electronic mail function is optional and is identified by symbol 15. As will be observed, Electronic Mail 15 is linked to Processing System 10 via link 15a. Although provision of the electronic mail is not an essential part of the invention hereof, its inclusion further increases the versatility of the system and may render it more useful in some applications.

As is well known to those of skill in the art, many processing systems contain substantial memory storage capacity, and the system hereof advantageously employs such memory storage capacity to record a number of important bodies of data and other information. Some of such data and information are represented by the cylinders in FIG. 1. These may either be a part of the memory of the processing system 10 or may be in other data banks that are accessible to the processing system 10.

Although the system hereof in its preferred form contemplates the use of magnetically encoded personnel identification cards, identification of personnel may, of course, be made manually and appropriate information entered into the system manually. In contemplation of at least the optional use of magnetically encoded cards, including conventional credit cards, there is provided access to a memory storage file that includes a listing of bad credit cards as represented by Bad Credit Card File 16. Zip Code File 17 may be optionally included so as to facilitate location, identification and other processing that may be expedited through zip code use.

For situations in which an insurance company is involved, relevant insurance company information and benefits as represented by Insurance Company File 18. Examples of pertinent information in such File 18 include the identification of covered illnesses and procedures, limits on insurance company payments for various illnesses and procedures, treatments and procedures for which utilization review is required, and treatments and procedures for which second opinions are necessary.

Since the system hereof contemplates compatibility with conventional insurance provisions that include patient deductibles, co-insurance by patient or another company and various other considerations that require selected individualized historical and other data to be recorded for each participant, system memory either includes or has access to files for each person as denoted by the Insured File 19. Somewhat similar considerations apply with respect to Claims File 20. There is stored detailed information covering relevant items of interest in ensuring accurate administration of claims in accordance with applicable criteria. Included are items such as those relating to claims histories, claims under review and claims in process.

Further reference to FIG. 1 reveals the inclusion of a smart system 21 including parameters dealing with diagnostics and drugs (as hereinafter described), an Employer File 21a which is indicative of those employee data which affect operation and implementation of the Wellness Health Management System. Examples are employee identification data such as employee identification numbers, length of service where such length of service affects participation in and coverage under the System, coverage for dependents, and similar items. Also included may be data identifying relevant employer parameters such as retention by the employer of review of selected treatments selected for implementation, employer override, preapproved monetary levels of authorization and the like. As will be evident from further consideration of FIG. 1, some of the above-described data may be contemplated by either the Insured File 19, the Employer File 21a, or both.

As will be perceived by those skilled in the art, many of the principles embodied in the Wellness Health Management System are applicable to individuals as well as groups. Others of the principles render the System even more attractive to specialized groups such as employees of a company or other organization. Accordingly, it will be recognized that pertinent data needed for implementation of the system will correspondingly vary, and the groupings of data identified in FIG. 1 are set forth for illustrative purposes and are not intended to suggest that all of such data are required in every instance in order to implement the principles hereof.

It is deemed well-known that although some groups of persons are self-insured (e.g., companies that themselves accept the risk and directly make payment to health providers), most companies and other organizations that provide health coverage for their employees do so through outside organizations, usually insurance companies. Accordingly, FIG. 1 includes, in addition to Insurance Company File 18, indicia 22 representing a check by the System to determine if a prospective participant (e.g., patient), has insurance company coverage, and, if so, any relevant particulars.

In addition to Insurance Company File 18 and Insurance Check indicia 22, there are shown communication links leading from Processing System 10 via path 23 to one or more insurance companies represented by rectangles 24a–24c. Such links integrate relevant insurance companies into the system according to the level of integration desired by the insurance company or companies. Of course, it will be evident that this also contemplates the integration, to the extent that is relevant, of self-insured companies and groups other than employees of a particular company.

Communication links 25 and 26 are provided to illustrate communication between Insurance Companies 24a-24c with Banks/Financial Institutions 27 and Employer(s) 28; and link 29 illustrates direct intercommunication between Banks/Financial Institutions 27 and Employer 28. Link 28a is provided to illustrate the communication link between Employer 28 and Processing System 10; and communication link 27a illustrates the communication link between Banks/Financial Institutions 27 and Processing System 10.

As mentioned above, one of the features hereof resides in the integration of the full spectrum of health care parameters including preventive profiles and regimens, the addressing of diseases and other health-impairing incidents when they do occur, and the addressing of post-treatment matters as necessary or desirable. Accordingly, FIG. 1 includes reference to Preventive Health Procedures 30 linked to Processing System 10 via link 31, and Post Treatment Procedures 32 linked to Processing System 10 via link 33.

As mentioned above, another of the features of the invention is represented by the cylinder 21 "Smart Systems—Drugs/Diagnostics". Such a smart system is contemplated by several of the following operations including that identified by rectangle 34 which is denominated "Utilization Review/Second Opinion/Procedure Approval". As will be evident from the ensuing description, the System is very versatile in that it can be tailored to include either or both of the Utilization Review and Second Opinion according to applicable criteria such as may be established, for example, by an employer, insurance company or group administration. Accordingly, rectangle 34 is shown as being linked by link 35 to an employer (if applicable), and by link 36 through Processing System 10 to other elements of the overall System.

Still another of the features of the invention is the optional integration of ancillary services into the System. As further mentioned herein, by ancillary services is meant the totality of supporting services that are needed to support total health. Such services include those of pharmacists, prosthesis providers, dentists, optometrists, audiologists and other medical specialists, laboratories and the like. Such services are represented by Ancillary Services rectangle 37 that is shown as being linked into the System through Processing System 10 through link 38. Other features are depicted by Patient Discharge Monitoring and Planning (linked to Processing System 10 through link 40), and Quality Control 41 (linked to Processing System 10 through link 42.

The Physician File 44 is provided to represent several classes of information and data that are useful in practicing the principles of the invention. While some of these data and information may be included elsewhere in the System so long as they are generally accessible therein, it may be convenient to describe them as if included within the Physicians File 44. Accordingly, the following references to such data and information should be understood to contemplate the physical location of such data in other sites as well as, or in addition to, files at the physician's location.

In accordance with the "Smart System" characteristics of the invention, Physician File 44 preferably will include an identification of the most commonly encountered diseases and other ailments, together with symptoms usually associated therewith. Accordingly, if symptoms are entered into the system terminal (e.g., one of terminals 11a–11c), and an identification of the corresponding illness is requested from the Processing System 10, the physician's file is interrogated, and the system prepares a list of the most likely medical condition corresponding to such symptoms, together with the generally approved and/or recommended treatment protocols. It also contemplates the identification within Physician File 44 of those procedures for which Utilization Review and/or Second Opinion 34 are deemed necessary or desirable.

In addition to the foregoing, Physician File 44 may optionally include other data or items of information. Thus, each individual physician may tailor a portion of his file to include additional items which reflect his own style and preferences.

Figure 2:
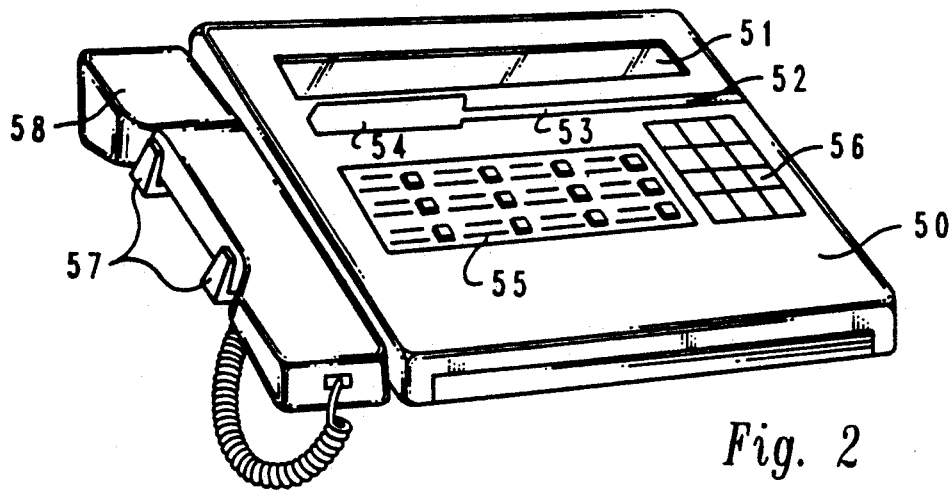
FIG. 2 is a perspective view illustrating a typical manual and data card entry terminal for use in the Wellness Health Management System.

Now turning to FIG. 2, it will be observed that it depicts, in a perspective view, a terminal suitable for utilization in the System as identified by symbols 11a-11c in FIG. 1. Although as mentioned above, all of the features of the illustrated terminal are not required in order to practice the principles of the invention and thus some of them are optional, it is deemed apparent that each of the features illustrated are attractive and add to the usefulness of the terminal.

The terminal of FIG. 2 includes a main housing 50 having a visual display window 51, a card data entry slot 52 having an elongated portion 53 and an enlarged portion 54, conventional manual data entry keyboard 55 and 10-key numeric calculator 56. It also includes conventional telephone handset cradle 57 and telephone handset 58. As will be evident from reference to FIG. 2, the terminal is operative in accordance with techniques well known in the data processing arts. Thus, for example, manual entry of information may be made by depressing the appropriate keys on keyboard 55, and information entry may also be made by inserting a conventional or special data-containing card (e.g., a "swipe card") into data entry slot 52 and moving it laterally therethrough. Although not necessary to the practice of the invention hereof, it is contemplated that the terminal will be responsive to data entry through conventional credit cards as well as special cards that may be issued for such purpose. It is also contemplated that the terminal may be adapted for reading bar codes such as those conventionally employed for identifying merchandise.

Figure 3:
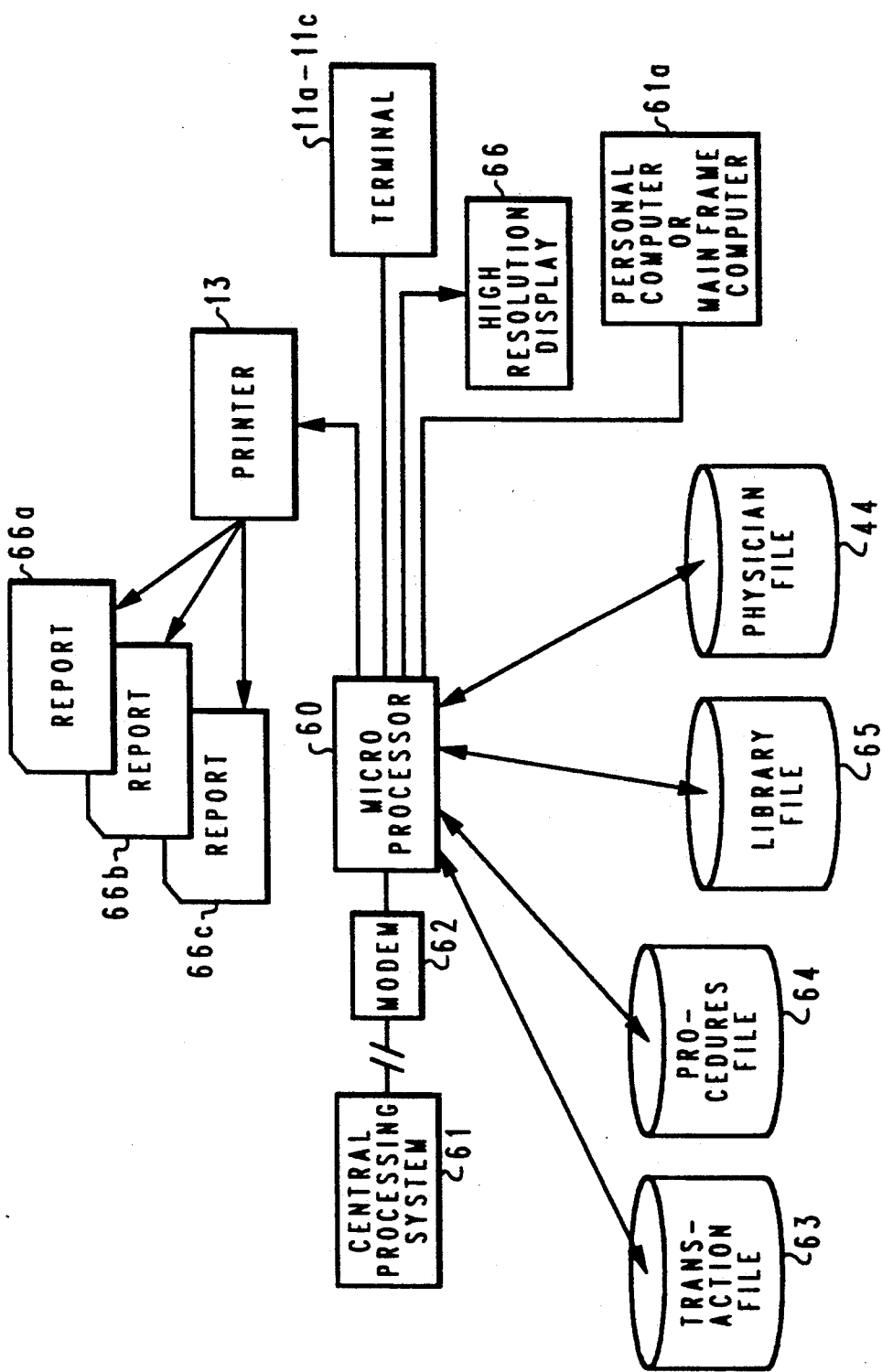
FIG. 3 is a block diagram depicting selected elements of the improved Wellness Health Management System when deployed in a distributed processing environment.

Now turning to FIG. 3, it will be observed that it illustrates practice of the principles hereof in a distributed processing environment. Thus, according to FIG. 3, a portion of the processing system 10 of FIG. 1 may be embodied in micro processor 60 and the remaining portion of the Processing System 10 in one or more other processors such as central processing system 61, or a personal computer or main frame computer as identified by rectangle 61a. Communication between system 61/61a and processor 60 is preferably conducted through one or more conventional modems represented by rectangle 62. In addition, although the files described above in connection with FIG. 1 may be provided within remote memory (e.g., memory within system 61), it is contemplated that at least a portion of such memory is resident physically at or in proximity to terminal(s) 11a-11c within the physician's office. Accordingly, the transaction file 63, procedures file 64 and library file 65 are shown as connected to the microprocessor 60 (rather than central processing system) for illustrative purposes only and not as requiring them to be physically resident at the physician's offices.

FIG. 3 also illustrates another feature mentioned above, namely, the provision of an optional high resolution display 66 preferably located in the physician's office so as to permit on-line real time display and visual review of relevant data, test results and the like. Also included &re representations 66a-66c which are illustrative of various reports that may be printed out or otherwise prepared in hard copy form by printer 13.

Figure 4:
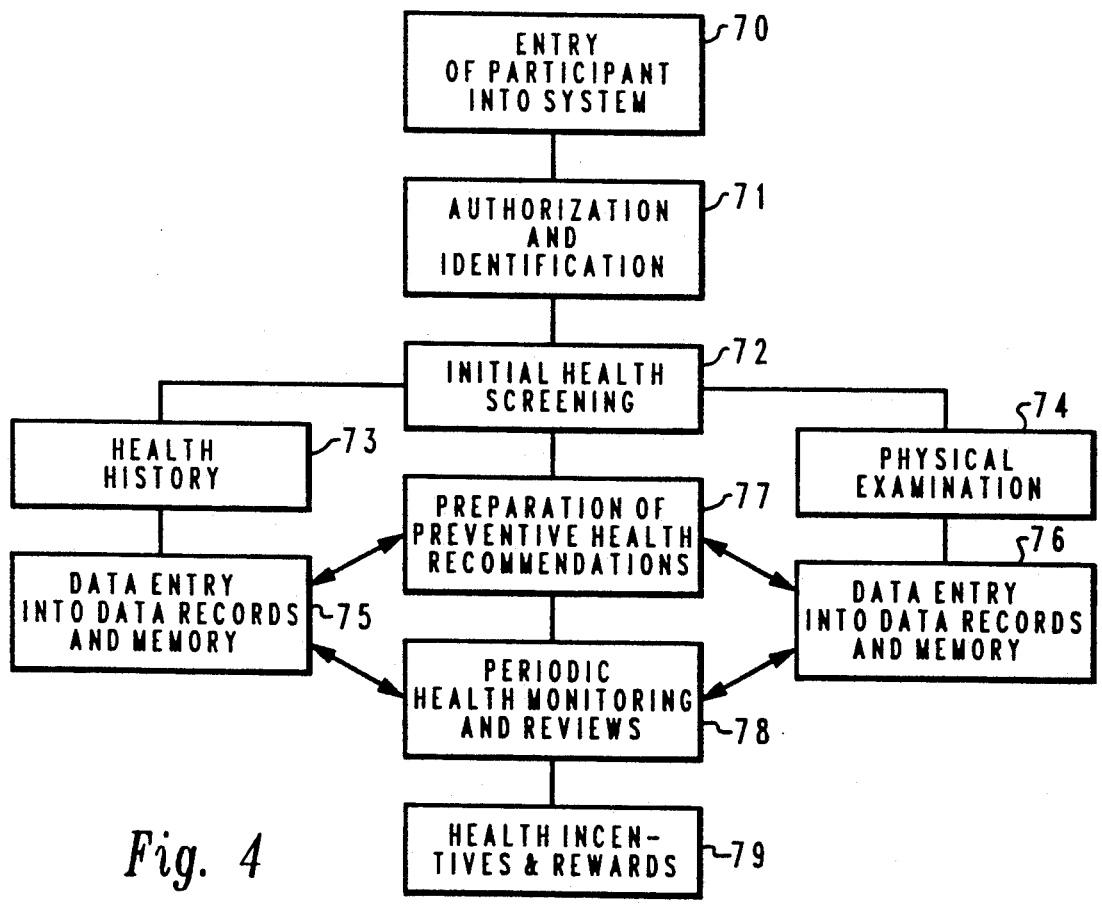
FIG. 4 is a diagram illustrating process flow of the preventive health portion of the System.

Now turning to FIG. 4, the preventive health aspect of the Wellness Health Management System is illustrated. There, it will be observed, is the entry of information for each participant into the System. This is symbolized by rectangle 70. Authorization and Identification 71 are made by designees such as authorized personnel within a company personnel department or an appropriate official within an insurance company. Once authorized, a participant is provided with an appropriate identification and/or other indicia which is subsequently used by the System to verify his authorization to participate as well as to identify his records and other information and data utilized by the System in carrying out its functions.

Next, it is contemplated that health screening is conducted as indicated at Initial Health Screening 72. Such initial health screening ordinarily includes recording health history 73 and a physical examination 74. As denoted by Data Entry items 75 and 76, relevant items of information are entered into System memory and/or manual records.

Based upon physician review (not depicted), health history 73 and physical examination information 74, preventive health recommendations 77 are prepared and presented to the participant. Such recommendations ordinarily include any pertinent changes in life style such as a change in diet, elimination of smoking, reduction or elimination of alcohol and drugs, reduction in weight, participation in prescribed physical exercise programs, reduction in blood pressure and the like. These are then communicated to the participant. This may be accomplished in any convenient way, for example by report printout such as reports 66a-66c of FIG. 3, oral communication, or both.

After preventive health recommendations have been communicated to the participant, provision is made for periodic monitoring and review 78. Such monitoring may take any of a variety of forms such as voluntary participation in tests, checking in to exercise areas by semiautomatic verification such as engaging an identification card with an appropriate reader, automatic identification of a participant by known sensing mechanisms appropriately located on an oval running track to account the number of times a participant has traversed the track, and the like. A variety of other monitoring techniques will also be evident to those skilled in the art.

In addition to the foregoing, health incentives and rewards 79 may be included in the preventive health portion of the System. Thus, for example, bonuses may be credited to participants according to the extent to which they adhere to their personalized recommended preventive health program or to the extent to which their own personal draw upon health resources falls below specified levels.

Figure 5:
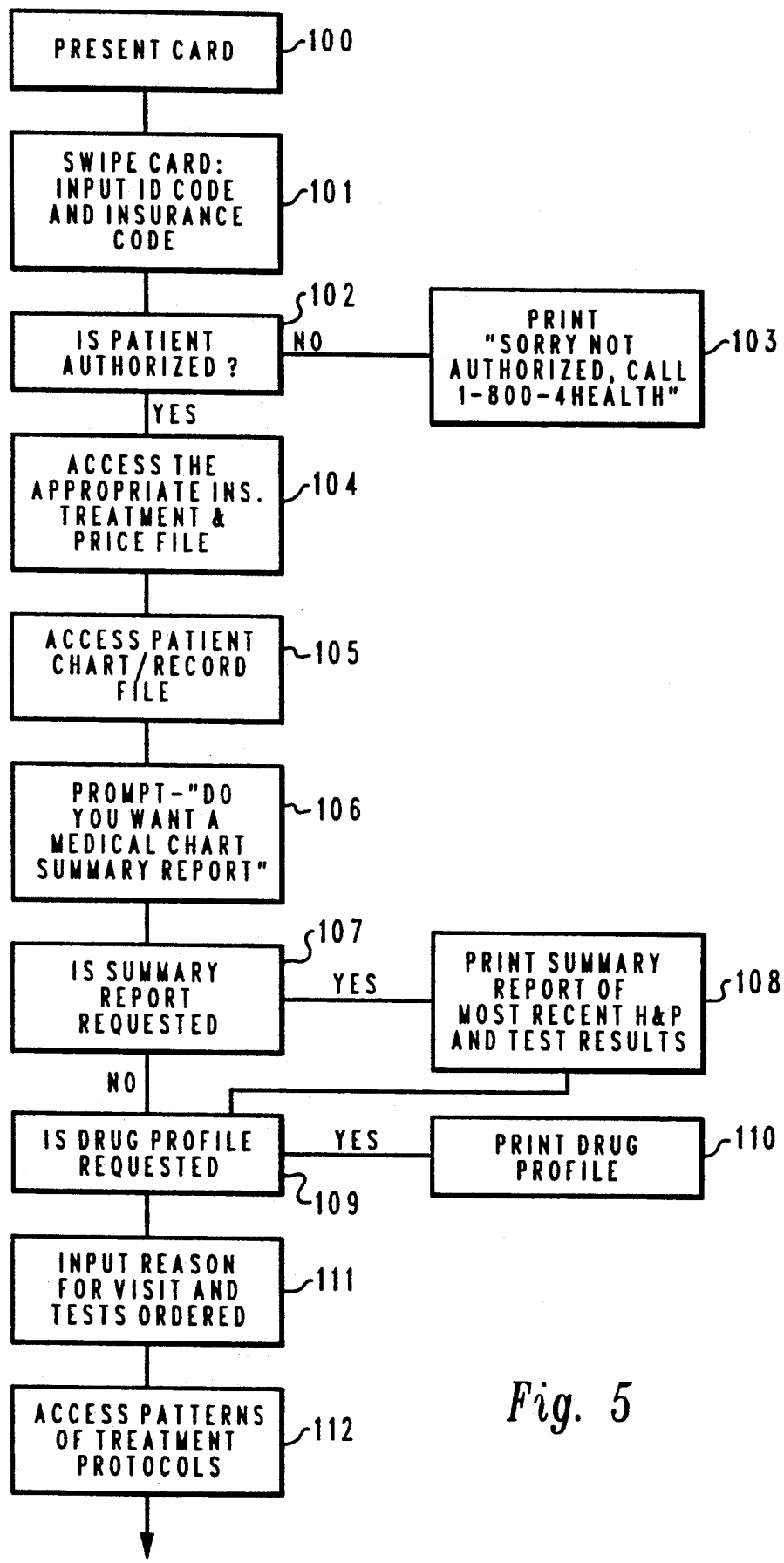
FIG. 5 is a diagram illustrating process flow of the diagnosis and treatment portion of the System.

Now turning to FIG. 5, it will be observed that it illustrates process flow of the diagnosis and treatment portion of the System. This portion, as with others, contemplates that the participant first be identified as one who is authorized to participate at some predetermined level of participation and financial support. Accordingly, this portion of the System includes an appropriate introduction of identifying information. Although as mentioned above, such introduction may be made manually as per one of the above-described terminals 11a-11c, the System preferably contemplates the use of a data card such as one that is encoded magnetically or one that contains conventional bar codes. Thus, the first element of FIG. 5 is the presentation of appropriate identification as represented by Present Card 100. Next, data is introduced into the System as indicated by Swipe Card Input ID Code and Insurance Code 101. This information is then processed by the Processing System 10 of FIG. 1 or corresponding microprocessor 60 and/or central processing system 61 of FIG. 3, accessing identification information as necessary or desirable from attendant files 44 (FIG. 3), and/or files 18-22 (FIG. 1) . Such information is utilized to verify the identification of the applicant and the authorization of the applicant to participate in the system as denoted by Is Patient Authorized rectangle 102. It also identifies to the System information and parameters for the System to perform its remaining functions as will be more evident from the following description.

If verification by the System reveals that the applicant is not authorized to participate, then an indication thereof is produced. This may take any of a variety of forms such as a visual or audible indication. Such an indication is represented by the rectangle 103 which contains the illustrative message Print "Sorry Not Authorized, Call 1-800-4Health". Of course, other indicia may be produced by the System as desired to tailor the System to the desires of the using physician and/or his staff.

If, as would normally be expected, the System verifies the authenticity and right to participate by the applicant, it then proceeds with its aforementioned accesses of information and parameters for the system to perform its remaining functions. Included are the accessing of the appropriate insurance or other basis for participation, the schedule for treatments and the prices thereof. This is indicated by rectangle 104. Also accessed are the participant's (patient's) charts and historical records. This is indicated by rectangle 105. As mentioned above, patient's medical charts and records are preferably stored in the physician's files 44 (FIGS. 1 and 3).

In order to expedite physician/staff review, provision is made to optionally produce a summary report. This is denoted by rectangle 106 Prompt "Do you want a Medical Chart Summary Report." If the summary report is requested as noted at 107, the report is then displayed either by visual display (e.g., display 66) or printed out as noted by rectangle 108 "Print Summary Report of Most Recent H&P and Test Results."

Continuing with operation of the System, it will be observed that it provides for accessing of drug profiles. Thus, the System asks "Is Drug Profile Requested" as denoted by rectangle 109. If the answer is "Yes", then the appropriate drug profile is displayed and/or printed as denoted by rectangle 110.

At this point in System operation, it is contemplated that information identifying the reason for the visit be entered and that any relevant tests be ordered. This is indicated by rectangle 111. Next, is shown "Access Patterns of Treatment Protocols 112. By this is contemplated the entry of symptoms and other data which can assist in making a diagnosis and identifying the aforementioned recommended treatment protocols. Thus, the physician is assisted in correlating the observed patient symptoms and test results so as to identify the most likely causes of the health problem, complete his diagnosis, and prescribe the most appropriate treatment protocols.

Figure 6:
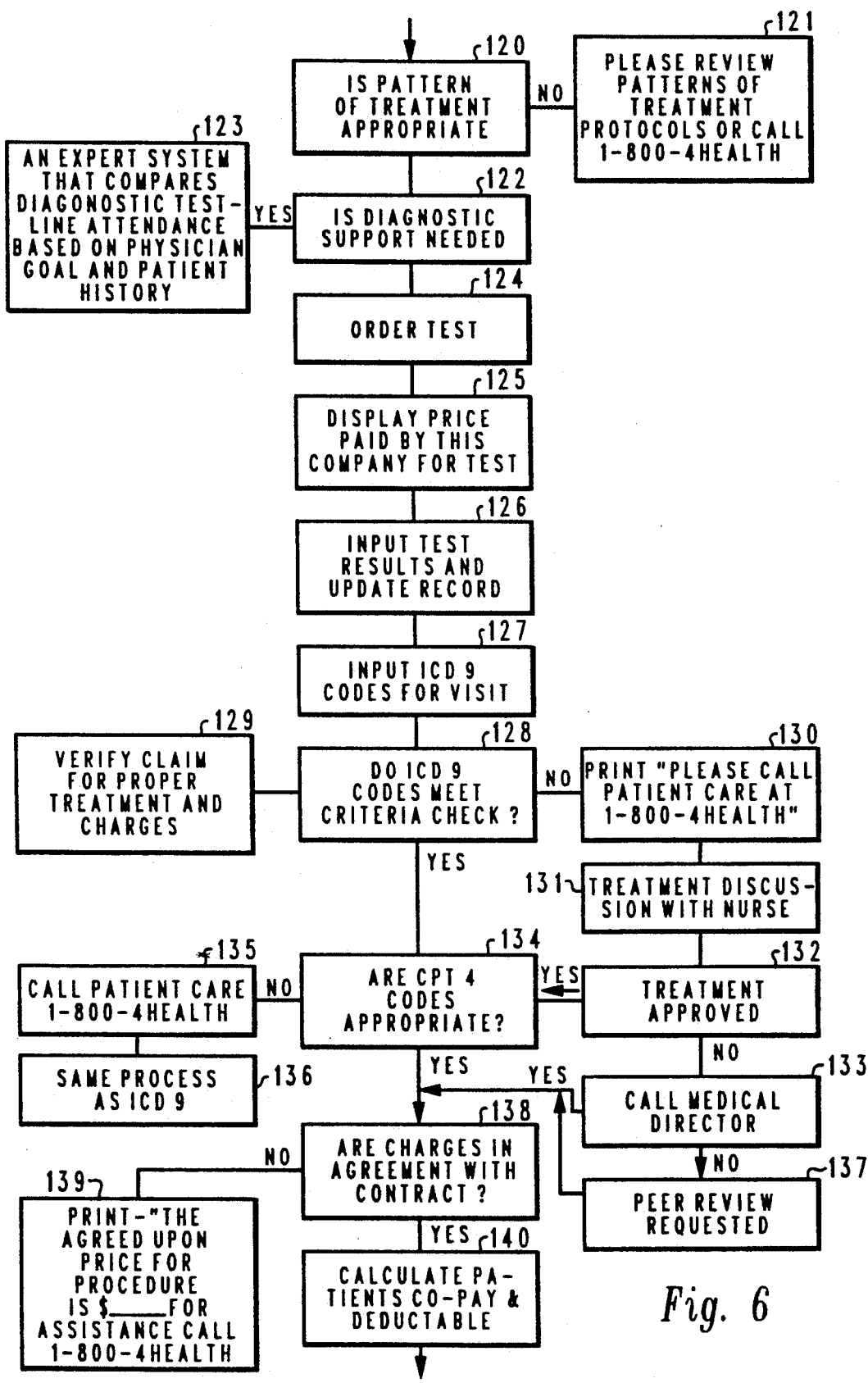
FIG. 6 is a continuation of the process flow of FIG. 5.
Figure 7:
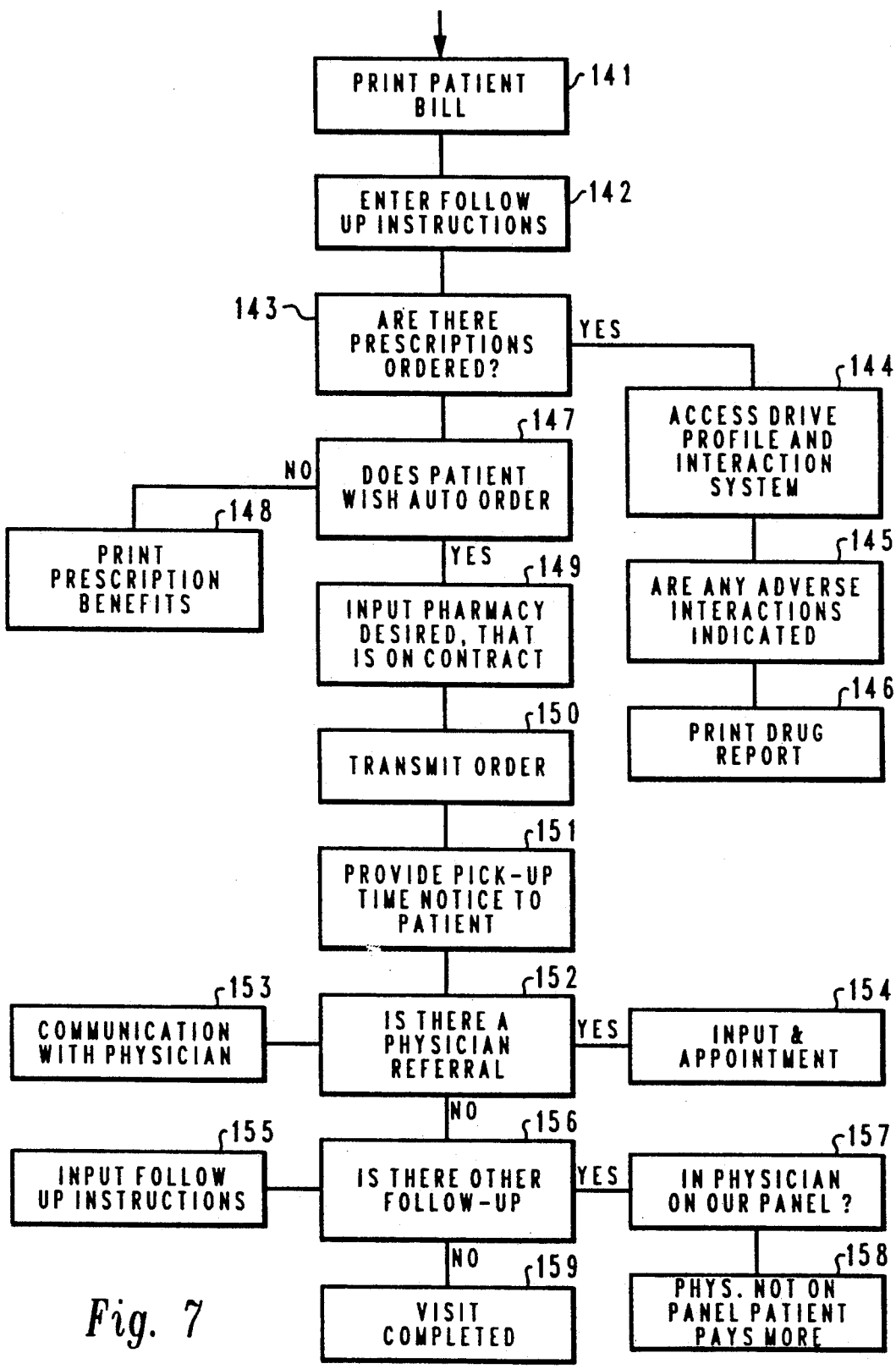
FIG. 7 is a continuation of the process flow of FIG. 6.

Further reference to the drawings reveals that FIG. 6 is a continuation of FIG. 5. Accordingly, reference to the upper portion of FIG. 6 reveals that next, the System addresses the question as to whether a proposed pattern of treatment is appropriate. This is indicated by rectangle 120. The physician or staff member enters into the System data identifying the proposed pattern of treatment, whereupon, the System compares the proposed pattern of treatment with the aforementioned recommended treatment protocols and provides an indication of any problem differences.

If the answer to the question of appropriateness of the recommended treatment is no, then the System produces a visual indication thereof as, for example, either through the aforementioned display 66 (FIG. 3), or a printout as denoted by rectangle 121. The physician or supporting staff member thus has called to this attention any discrepancy between his proposed pattern of treatment and that which is generally recommended by recognized medical authorities.

In addition to the foregoing, the System also includes provision for further diagnostic support. This is indicated by rectangle 122 "Is diagnostic Suport Needed." If the answer is "No", then the system continues on as indicated. However, if the answer is "Yes", then the system invokes such additional assistance as indicated by rectangle 123 "An Expert System that Compares Diagnostic Testline Attendance Based on Physician goal and Patient History." Thus, the physician is able to determine the testing options based on conditions and the condition of the body that each test was designed to report on. In addition, the physician is given the cost of each testing procedure including those that are laboratory or radiology based. If requested, the system will allow the physician to select through a triage process to determine what test would yield the best data for diagnosis of the presenting problem.

As will be evident to one skilled in the art, a well-ordered system should provide for the ordering of tests by the attending physician at any point in its operation. Accordingly, although the ordering of tests is shown in the drawing at particular points, it should be understood that this is illustrative only and does not suggest that tests may not be ordered at other points during operation of the System.

The actual ordering of tests is identified by the Order Test rectangle 124. Tests may be ordered by separate orders levied on laboratories and the like by telephone, written documents or semi-automatically through operation of the System processor and communication by modem and the like. Thus, as earlier mentioned and as described below, supporting and ancillary services are integrated into the System and are effective to provide such ancillary services and support as are called for by the attending physician or other authorized staff personnel.

The capability for displaying various detailed information items may be included in the System. This is illustrated by inclusion of rectangle 125 which is labelled "Display Price Paid by this Company for Test." As mentioned previously, it is contemplated that a schedule of fees approved by the financial institution (e.g., insurance company) for various tests and procedures is stored within the appropriate memory bank(s). This schedule is accessed, and the approved fee for the specific procedure under consideration is displayed or otherwise communicated to the physician or supporting staff member.

After receiving the results of tests and/or other supporting services, the results are entered into the System. This may be performed either by manual keyboard entry or semi-automatically through the communication of appropriate information into the System electronically. This is denoted by rectangle 126 "Input Test Results and Update Record."

After the records have been updated to reflect any test results that maybe applicable, provision is made for the attending physician or authorized support staff member to review the diagnosis or proposed treatment protocols and either amend or confirm his proposed course of treatment.

As will be recognized by those skilled in the arts, it is customary for insurance companies and other health care financial organizations to utilize codes for identifying and determining approved criteria and the approved schedules of procedures and costs therefor or in accordance therewith. An example of such codes is the family of codes designated with the symbols ICD (an acronym standing for International Code of Disease based on Health Care Financing Administration official codes as published by the U.S. Department of Health and Human services in 1989.

Reference herein is also made to another standard set of codes known to those skilled in the art as CPT codes. The term CPT is an acronym derived from physicians' Current Procedural Terminology. These codes are standard treatment description and price file codes as set forth in the Amnerican Medical association compendium of Physicians Current Procedural Terminology. The current CPT is a listing of descriptive terms and identifying codes for reporting medical services and procedures performed by physicians.

In order to facilitate claims compliance with applicable criteria, ICD9 coded information is entered into the System to indicate various data relating to details of the incident (patient visit, treatment and the like). This is indicated by rectangle 127.

The System interrogates the Insurance Company (or other payor) files, e.g., file 18 in FIG. 1, and verifies that the ICD9 codes either meet or do not meet applicable criteria. This is noted by rectangle 128. In so doing, the expense associated with the incident is considered as a claim and is reviewed as noted by rectangle 129 "Verify Claim for Proper Treatment and Charges."

If, as noted in the drawing, the entered ICD9 codes do not meet the applicable criteria check (128), then a visual representation thereof is displayed or otherwise communicated to attending personnel as indicated by rectangle 130, whereupon, it is contemplated that there will ensue a treatment discussion with a nurse (or other appropriate persons) as noted by rectangle 131. Thereafter, a treatment protocol is either approved or disapproved as noted by rectangle 132. If disapproved, the System contemplates contact with the Medical Director or other cognizant authority as indicated by rectangle 133. On the other hand, if the treatment protocol is approved, the System then proceeds to an examination of CPT4 codes and checks to see if they are appropriate as noted by rectangle 134. If the System determines that the CPT4 code check is not met, the System so notes and displays or otherwise indicates that further checking is needed. This is indicated by rectangle 135 "Call Patient Care 1-800-4Health." Upon accessing rectangle 135, the System proceeds in a manner similar to that for implementing the checking of ICD9 codes. This is noted by rectangle 136

Now returning to rectangle 133, it will be observed that if the medical director does not approve or otherwise grant a variance so as permit proceeding with the treatment, then the System includes referral for peer review as noted by rectangle 137. Peer review results in a decision on the recommended course of treatment and results in the determination of whether or not the charges are in agreement with any applicable financial criteria such as whether or not the charges are in agreement with an insurance contract. This is denoted by rectangle 138. If the charges are found not to be in agreement with applicable criteria, then a visual manifestation, preferably a print-out, is provided. This is indicated by rectangle 139 Print "The Agreed Upon Price for Procedure is $__. For Assistance Call 1-800-4Health."

It will now be evident that the aforementioned Second Opinion feature is included by the System within the procedures set forth by the process flow depicted in the lower half of FIG. 6. Thus, if selected criteria are not met, they a proposed course of treatment or selected procedure are shown to require a second opinion as contemplated by reference to a medical director (rectangle 133) or one more peers (rectangle 137).

Returning to rectangle 138, if the charges are in agreement, then the System processor calculates any patient co-pay and/or deductible as noted by rectangle 140, and the printer 13 (FIG. 1) prints out a statement for the patient as noted by rectangle 141.. The System processor also records pertinent data and information into the above-described files, as needed. If System criteria require reference to or approval by an Employer, Insurance Company, or Financial Institution, the System processor (s) ensures that such is accomplished.

The attending physician or designee ensures that follow-up instructions, information and data are entered into the System as denoted by rectangle 142. This ordinarily includes an indication of any prescriptions that are to be ordered as noted by rectangle 143. If there are any, the System then accesses its drug profile in memory as noted by rectangle 144 and identifies any adverse interactions that may be indicated as noted by rectangle 145. The System printer (e.g., Printer 13 of FIG. 1) then prints out a drug report 146 which includes pertinent information relating to proposed drugs.

Next, the System addresses the question as to whether the patient wishes the prescribed drugs to be ordered automatically by the System as noted by rectangle 147. If not, the System printer (e.g., printer 13) prints out a description of prescription benefits 148 as an aid to the patient in his obtaining himself the indicated medications. On the other hand, if the answer is Yes, then the System accesses its aforementioned data bank to ascertain the identity of any approved ancillary provider (e.g., pharmacy as indicated by rectangle 149) and then automatically transmits the order and indicia (rectangle 150) identifying the medication to such ancillary provider as a basis for the provider to prepare the indicated medication. Included is a notice to the patient 151 to timely pick up the medication or otherwise arrange for its timely acquisition.

In order to provide for effective communication with others having a legitimate interest in any physician-patient interaction, provision is made for contact with any referring physician. This is noted by rectangle 152 in which the System makes inquiry of its data as to whether the patient was referred to the System by another physician or, conversely, whether there is not a referral by the attending physician to a specialist or another physician. If the patient was referred to the attending physician by another physician, appropriate feed-back information is communicated to the referring physician. This can accomplished by telephone report, electronic mail, or preferably by written hard copy print out as indicated by rectangle 153. On the other hand, if the patient is referred to another physician, provision is made for the making of an appointment and transmission of pertinent information to such other physician as noted by rectangle 154.

If there is no other physician referral, the System then accepts any Input Follow Up Instructions and prepares written communications thereof to the patient as noted by rectangle 155. If there are other follow ups as noted by rectangle 156, the System ensures that pertinent data and indicia are entered into pertinent files (including the System calendar) so that timely call-up can be made for monitoring and compliance. In addition, the System optionally determines whether the attending physician is a part of a relevant group of physicians as noted by rectangle 157. Ordinarily, if the attending physician is not part of the relevant group, some appropriate additional charge is made to reflect the relevant additional costs. This is indicated by rectangle 158.

When the visit or other contact (e.g., monitoring visit by attending physician to patient when hospitalized), an appropriate input is made to the System as denoted by rectangle 159. The System thus recognizes when the visit or other incident is completed and makes an appropriate record in its memory.

Figure 8:
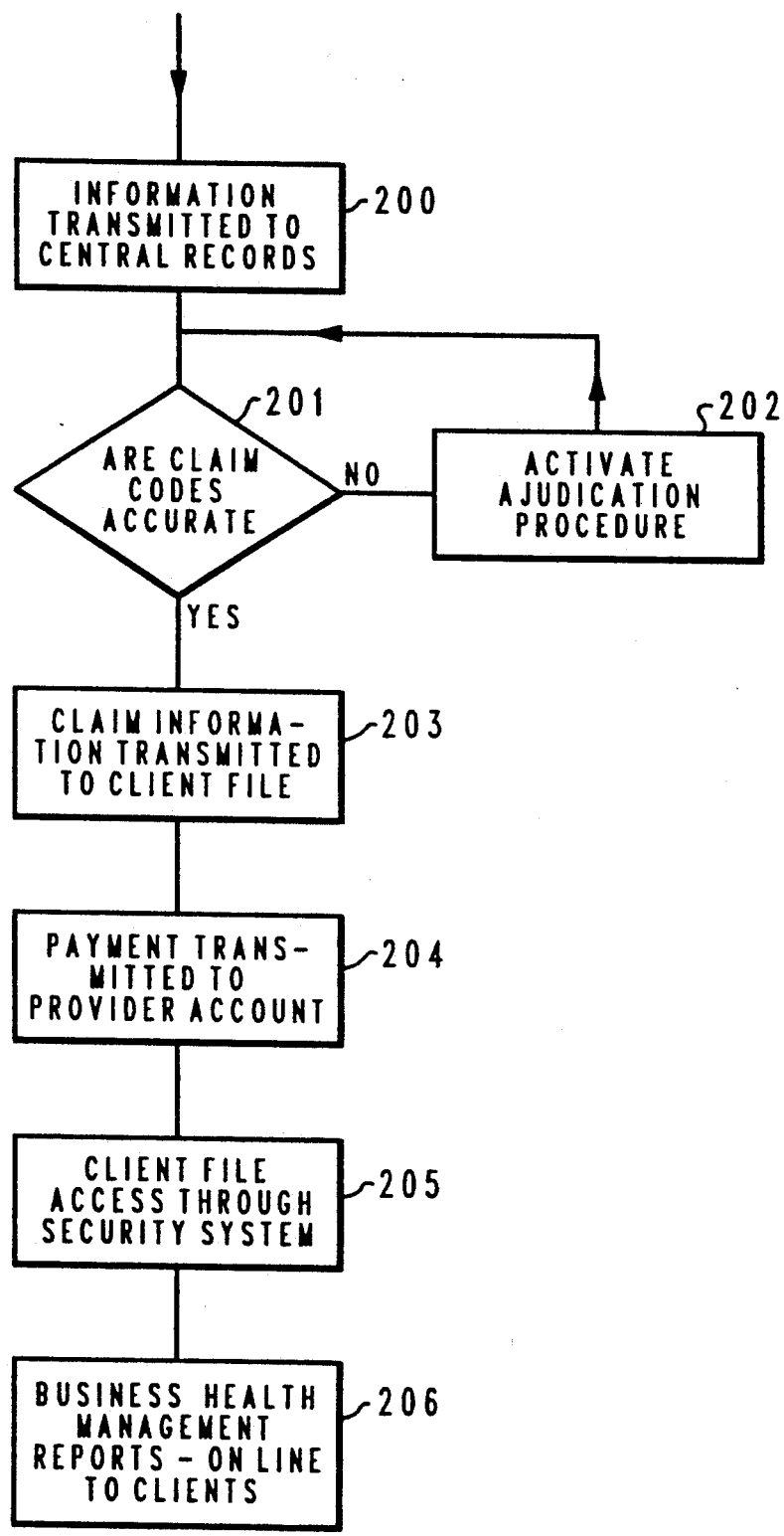
FIG. 8 is an adjunct to the process flow of FIGS. 5-7.

Now turning to FIG. 8, others of the features of the invention are depicted. There, the flow of information to central system records is indicated by rectangle 200. The System checks to ensure whether claim codes are accurate as noted by diamond 201. If no, the an adjudication procedure is activated as noted by rectangle 202. According to such adjudication procedure, review by one or more designated persons is made to ensure a high level of quality control and conformity with applicable criteria.

Upon regularization of claim codes, claim information is transmitted to a client file as noted by rectangle 203. By client is meant an employer, group manager, insurance company and the like. Concurrently with transmission of claim information to the client, provision is made for transfer to the account of the health provider (e.g., the attending physician, clinic or the like) of the approved sums for such claims as noted by rectangle 204. This can be accomplished in a variety of ways, depending upon the desires of the health provider, employer, insurance company, group administrator and financial institution (e.g., bank). Such transfer is identified in the disclosure of FIG. 1 and is described in connection therewith. Information as to such transfer also is communicated to the relevant client file through an appropriate security system as noted by rectangle 205. Business management reports, as desired, are prepared periodically and sent to clients as noted by rectangle 206.

Figure 9:
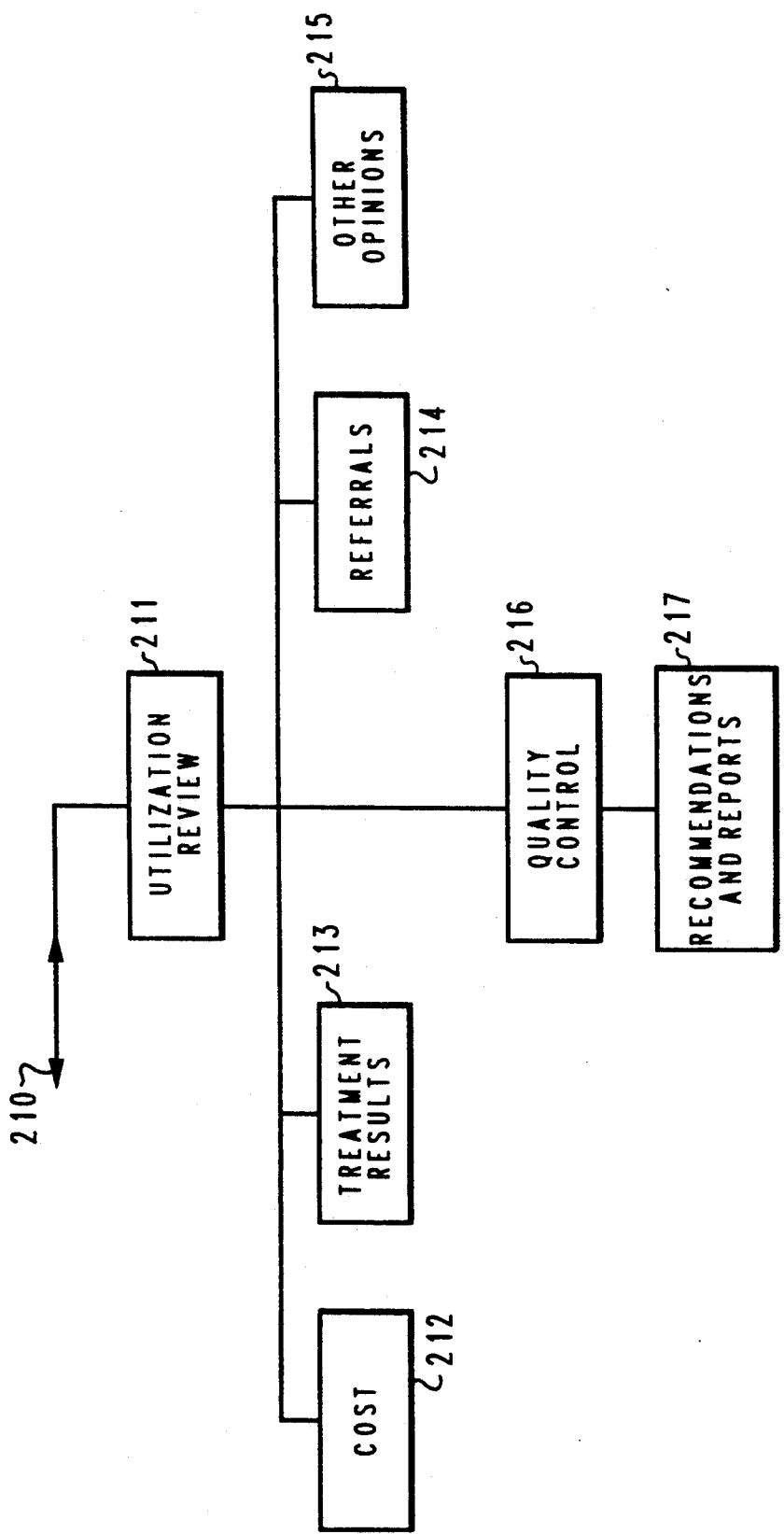
FIG. 9 is diagram illustrating the conclusion of the process flow of FIGS. 4-8.

FIG. 9 depicts aspects of the above-mentioned utilization review. According to a feature of the System, utilization review may be tailored to meet criteria established by one or more users of the System. Thus, selected levels of expense, types of procedures, length of expected hospitalization, specific illnesses, categories of illnesses or other criteria may be utilized to identify those items for which utilization review is indicated. Alternatively, or in addition, selected items may be selected at random for utilization review and quality control determination.

The point of connection to the flow diagrams of the foregoing Figures is discretionary. However, in accordance with the preferred embodiment, it is expected that the point defined by arrow 210 in FIG. 9 will connect into the remainder of the System at a point such as that identified by element 200 of FIG. 8. Thus in addition to information being transmitted to central records (as noted by rectangle 200), it also is made available to utilization review 211 (FIG. 9). As mentioned above, the System may be tailored to consider any of a variety of factors for review such as Cost 212, Treatment Results 213, Referral Matters 214, Other Opinions 215 and the like. From a review of the cost effectiveness of the item under consideration, factors indicative of Quality Control 216 may readily be calculated by the System using desired criteria. For example, the frequency of repeat consultations for the same health problem can be used as an indication or determinant of effectiveness of treatment. Moreover, from a study of System data, Recommendations and Reports 217 are generated to form the basis for future improvements.

Figure 10:
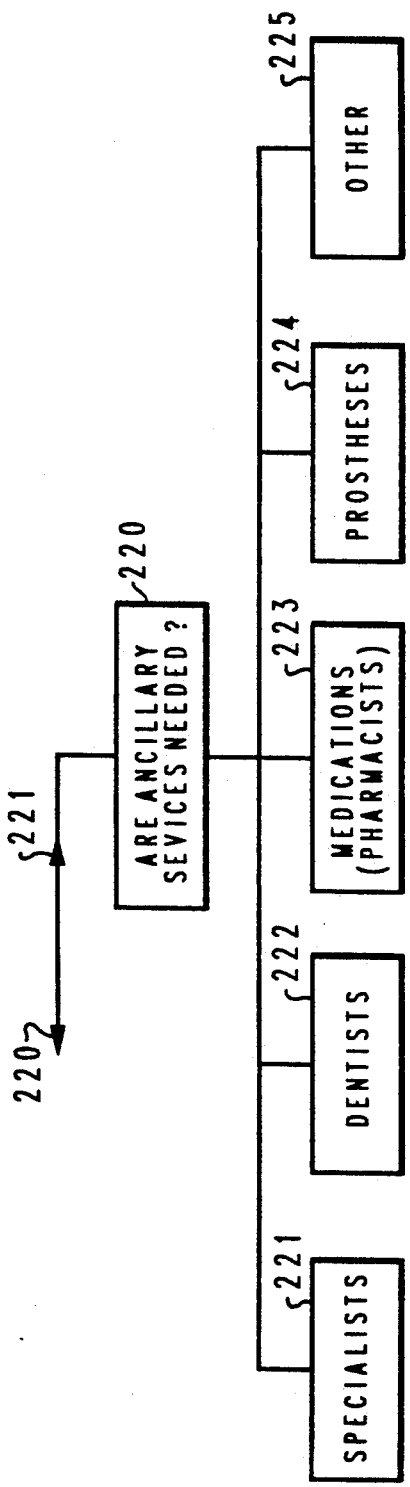
FIG. 10 is a diagram illustrating details of ancillary services.

FIG. 10 illustrates the aforementioned ancillary services in more detail. There, communication of ancillary needs is represented by arrows 220 and 221 which depict the two-way flow of information. As mentioned above, the System identifies the need for ancillary services by examining data and information relating to each participant (patient) as noted by rectangle 222 and calls such need to the attention of the attending physician or other designated authority. In the absence of entry to the contrary, the System communicates the need appropriately as described above to the indicated ancillary service, examples of which are Specialists 221, Dentists 222, Pharmacists 223 for Medications, Suppliers of Prostheses 224, and any others as represented by rectangle 225.

Figure 11:
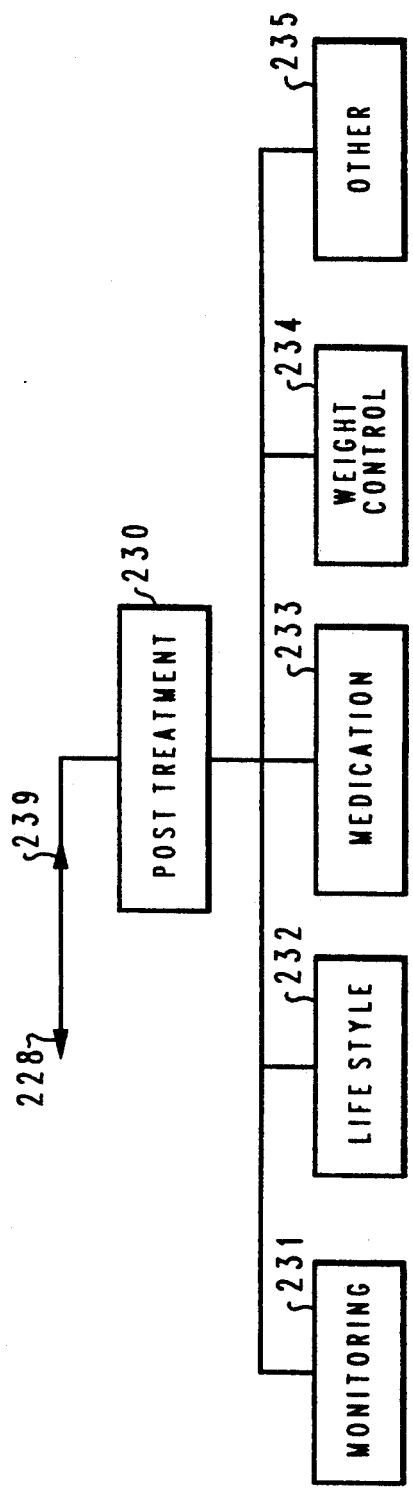
FIG. 11 is a diagram illustrating details of post treatment features of the invention.

FIG. 11 illustrates the aforementioned feature of Post Treatment matters. There, arrows 228 and 239 indicate the two-way flow of information to and from the principal flow paths as described above. Also as described above, the System determines from entered data, the need for Post Treatment matters 230 such as Monitoring 231, Life Style 232, Medication 233, Weight Control 234 and Other 235. Thus, operation of the System is extended to cover all relevant facets of health maintenance and control.

Although the invention hereof has been described by way of example of a preferred embodiment, it will be evident that other adaptations and modifications may be employed without departing from the spirit and scope thereof. For example, other types of distributed processing could be employed. Additionally, a wide variety of automatic transfer of funds could be employed as between providers, ancillary services, employers, insurance companies and the like.

The terms and expressions employed herein have been used as terms of description and not of limitation; and thus, there is no intent of excluding equivalents, but on the contrary it is intended to cover any and all equivalents that may be employed without departing from the spirit and scope of the invention.

What is claimed is:

1. A comprehensive health care management system comprising:
   (a) input means for entering data identifying each of a predetermined plurality of persons;

(b) a data bank memory interconnected with said input means, said data bank memory including an identification of predetermined procedures requiring utilization review;
(c) payment means; and
(d) means in communication with said input means responsive to input of data through said input means symbolic of symptoms of one of said predetermined plurality of persons for tentatively identifying a proposed mode of treatment for said one of said predetermined plurality of persons and, when said proposed mode of treatment includes one of said predetermined procedures requiring utilization review, for producing indicia indicative thereof and for preventing payment therefor by said payment means until said utilization review has been obtained and data indicative thereof has been entered in said system.

2. A comprehensive health care management system according to claim 1 in which said means responsive to the input of data symbolic of patient symptoms for tentatively identifying a proposed mode of treatment include means effective when said proposed mode of treatment includes an ancillary service, for producing indicia indicative thereof and for providing said ancillary service.

3. A comprehensive health care management system according to claim 1 in which said means responsive to the input of data symbolic of symptoms includes means for tentatively identifying preventive health routines for addressing each of any identified plurality of potentially health-destructive conditions including excessive weight, high blood pressure, smoking, and insufficient exercise.

4. A comprehensive health care management system comprising:
(a) input means for entering data identifying each of a predetermined plurality of persons and for entering data symbolic of patient symptoms;
(b) a first data bank memory interconnected with said input means, said first data bank memory containing predetermined items of medical history for said predetermined plurality of persons;
(c) another data bank memory interconnected with said first data bank memory, said another data bank memory including an identification of predetermined procedures requiring utilization review;
(d) payment means; and
(e) means interconnected with said payment means responsive to input to said system of said data symbolic of patient symptoms for tentatively identifying a proposed mode of treatment and, when said proposed mode of treatment includes one of said predetermined procedures requiring utilization review, for producing indicia indicative thereof and for preventing payment therefor by said payment means until said utilization review has been obtained and data indicative thereof has been entered in said system.

5. A comprehensive health care management system according to claim 4 in which said predetermined items of medical history include physical profiles of said predetermined plurality of persons.

6. A comprehensive health care management system according to claim 4 in which said input means further includes a data input terminal for entering into said system said predetermined items of medical history.

7. A comprehensive health care management system according to claim 4 in which said data input terminal is responsive to inputs thereto to enter into one of said data banks data severally identifying said predetermined plurality of persons.

8. A comprehensive health care management system according to claim 7 further including means for verifying authenticity of identifications of said predetermined plurality of persons.

9. A comprehensive health care management system according to claim 8 further including means for verifying eligibility for treatment of said predetermined plurality of persons.

10. A comprehensive health care management system according to claim 9 wherein said means for verifying the eligibility for treatment of said predetermined plurality of persons further includes means for identifying preselected classes of treatments to be pre-certified for authorized treatment and payment.

11. A comprehensive health care management system according to claim 4 in which said data input terminal includes provision for data entry from a magnetically-encoded medium.

12. A comprehensive health care management system according to claim 4 in which said data input terminal includes provision for data entry from a manual keyboard.

13. A comprehensive health care management system according to claim 2 in which one of said data bank memories includes identification of symptoms for diagnosis of each of a predetermined plurality of illnesses.

14. A comprehensive health care management system according to claim 2 in which one of said data bank memories includes data representing treatment for each of a predetermined plurality of illnesses.

15. A comprehensive health care management system according to claim 13 in which one of said data bank memories includes data representing treatment for each of said predetermined plurality of illnesses.

16. A comprehensive health care management system comprising:
(a) input means for entering data identifying each of a predetermined plurality of persons;
(b) a data bank memory interconnected with said input means, said data bank memory including an identification of predetermined procedures requiring second options;
(c) payment means; and
(d) means in communication with said input means responsive to input of data through said input means symbolic of symptoms of one of said predetermined plurality of persons for tentatively identifying a proposed mode of treatment for said one of said predetermined plurality of persons and, when said proposed mode of treatment includes one of said predetermined procedures requiring a second opinion, for producing indicia indicative thereof and for preventing payment therefor by said payment means until a second opinion has been obtained.

17. A comprehensive health care management system according to claim 16 in which said means responsive to the input of data symbolic of symptoms for tentatively identifying a proposed mode of treatment include means effective when said proposed mode of treatment includes an ancillary service, for producing indicia indicative thereof and for providing said ancillary service.

18. A comprehensive health care management system according to claim 16 in which said means responsive to the input of data symbolic of symptoms includes means for tentatively identifying preventive health routines for addressing each of any identified plurality of potentially health-destructive conditions including excessive weight, high blood pressure, smoking, and insufficient exercise.

19. A comprehensive health care management system comprising:
(a) input means for entering data identifying each of a predetermined plurality of persons and for entering data symbolic of patient symptoms;
(b) a first data bank memory interconnected with said input means, said data bank memory containing predetermined items of medical history for said predetermined plurality of persons;
(c) another data bank memory interconnecting with said first data bank memory, said another data bank memory including an identification of predetermined procedures requiring second opinions;
(d) payment means; and
(e) means interconnected with said payment means responsive to the input to said system of said data symbolic of patient symptoms for tentatively identifying a proposed mode of treatment and, when said proposed mode of treatment includes one of said predetermined procedures requiring a second opinion, for producing indicia indicative thereof and for preventing payment therefor by said payment means until a second opinion has been obtained.

20. A comprehensive health care management system according to claim 19 in which said predetermined items of medical history include physical profiles of said predetermined plurality of persons.

21. A comprehensive health care management system according to claim 19 in which said input means further includes a data input terminal for entering into said system said predetermined items of medical history.

22. A comprehensive health care management system according to claim 19 in which said data input terminal is responsive to inputs thereto to enter into one of said data banks data severally identifying said predetermined plurality of persons.

23. A comprehensive health care management system according to claim 22 further including means for verifying authenticity of identifications of said predetermined plurality of persons.

24. A comprehensive health care management system according to claim 23 further including means for verifying eligibility for treatment of said predetermined plurality of persons.

25. A comprehensive health care management system according to claim 24 wherein said means for verifying eligibility for treatment of said predetermined plurality of persons further includes means for identifying pre-selected classes of treatments to be pre-certified for authorized treatment and payment.

26. A comprehensive health care management system according to claim 19 in which said input means includes provision for data entry from a magnetically-encoded medium.

27. A comprehensive health care management system according to claim 19 in which said input means includes provision for data entry from a manual keyboard.

28. A comprehensive health care management system according to claim 17 in which one of said data bank memories include identification of symptoms for diagnosis of each of a predetermined plurality of illnesses.

29. A comprehensive health care management system according to claim 17 in which one of said data bank memories include data representing treatment for each of a predetermined plurality of illnesses.

30. A comprehensive health care management system according to claim 28 in which one of said data bank memories include data representing treatment for each of said predetermined plurality of illnesses.

31. A comprehensive health care management system comprising:
(a) a data input terminal for entering data identifying each of a predetermined plurality of persons being on a payroll of an organization;
(b) a data bank memory containing predetermined items of medical history for said predetermined plurality of persons;
(c) payroll deduction means for providing payment for said predetermined plurality of persons;
(d) another data bank memory including an identification of predetermined medical procedures and pre-approved levels of payments for said predetermined medical procedures; and
(e) means responsive to input of data indicative of performance of one of said predetermined medical procedures for one of said predetermined plurality of persons for examining a level of charge made by a provider of medical services for the performed procedure and, if said level of charge exceeds the pre-approved level of payment for said procedure, for causing said payroll deduction means to pay the exceeded amount by payroll deduction.

32. A comprehensive health care management system comprising:
(a) a first data input terminal at the location of a medical services provider for entering data identifying each of a predetermined plurality of persons being on a payroll of an organization;
(b) a second data terminal at the location of said organization;
(c) a first data bank memory containing predetermined items of medical history for said predetermined plurality of persons;
(d) another data bank memory including an identification of predetermined medical procedures and pre-approved levels of payments for said predetermined medical procedures; and
(e) means responsive to input of data indicative of performance of one of said predetermined medical procedures for one of said predetermined plurality of persons and for examining a level of charge made by a provider of medical services for the performed procedure and, if said level of charge exceeds the pre-approved level of payment, for producing at the location of said second data terminal indicia indicative thereof and for permitting authorization for the excess to be made by said organization.

33. A comprehensive health care management system comprising:
(a) a data input terminal for entering data identifying each of a predetermined plurality of persons being subject to workmen's compensation;
(b) a data bank memory including an identification of predetermined medical procedures and preapproved levels of workmen's compensation payments for said predetermined medical procedures; and (c) means responsive to the input of data to said system indicative of the desirability of performance of one of said predetermined medical procedures for one of said predetermined plurality of persons for examining a level of charge made by a provider of medical services for the performed procedure and, if said level of charge exceeds the pre-approved 34. A comprehensive health care management system comprising:
(a) input means for entering data identifying each of a predetermined plurality of persons and for entering data symbolic of patient symptoms;
(b) a first data bank memory interconnected with said input means, said first data bank memory containing predetermined items of medical history for each of said predetermined plurality of persons;
(c) another data bank memory interconnected with said first data bank memory, said another data bank memory including an identification of predetermined procedures requiring ancillary services; and
(d) means interconnected with said another data bank memory and responsive to the input to said system of said data symbolic of patient symptoms for tentatively identifying a proposed mode of treatment and, when said proposed mode of treatment includes one of said ancillary services, for producing indicia indicative thereof and for providing said one of said ancillary services.

35. A comprehensive health care management system according to claim 34 in which said predetermined items of medical history include physical profiles of said predetermined plurality of persons.

36. A comprehensive health care management system according to claim 34 in which said input means further includes a data input terminal for entering into said system said predetermined items of medical history.

37. A comprehensive health care management system according to claim 34 in which said input means includes a data input terminal responsive to inputs thereto to enter into one of said data banks data severally identifying said predetermined plurality of persons.

38. A comprehensive health care management system according to claim 34 further including means for verifying authenticity of identifications of said predetermined plurality of persons.

39. A comprehensive health care management system according to claim 34 further including means for verifying eligibility for treatment of said predetermined plurality of persons.

40. A comprehensive health care management system according to claim 39 wherein said means for verifying the eligibility for treatment of said predetermined plurality of persons further includes means for identifying pre-selected classes of treatments to be pre-certified for authorized treatment and payment.

41. A comprehensive health care management system according to claim 34 in which said means responsive to the input of data symbolic of patient symptoms includes means for tentatively identifying preventive health routines for addressing each of any identified plurality of potentially health-destructive conditions including excessive weight, high blood pressure, smoking, and insufficient exercise.

42. A comprehensive health care management system according to claim 37 in which said data input terminal includes provision for data entry from a magnetically-encoded medium.

43. A comprehensive health care management system according to claim 37 in which said data input terminal includes provision for data entry from a manual keyboard.

44. A comprehensive health care management system according to claim 34 in which one of said data bank memories includes identification of symptoms for diagnosis of each of a predetermined plurality of illnesses.

45. A comprehensive health care management system according to claim 34 in which one of said data bank memories includes data representing treatment for each of a predetermined plurality of illnesses.

46. A comprehensive health care management system according to claim 44 in which one of said data bank memories includes data representing treatment for each of said predetermined plurality of illnesses.

47. An integrated health care management system comprising:
(a) a data input terminal for entering data identifying each of a predetermined plurality of persons;
(b) a data bank memory containing predetermined items of medical history including physical profile data for said predetermined plurality of persons;
(c) health regimen recommendation means responsive to said physical profile data for said predetermined plurality of persons for generating individualized preventive health regimen recommendations for said predetermined plurality of persons including diet and exercise;
(d) symptom recording means including said data bank memory for recording symptoms associated with each of a predetermined plurality of health problems;
(e) recommend treatment means including said data bank memory for recording recommended treatment for each of said predetermined plurality of health problems;
(f) utilization review means including said data bank memory for selecting and recording identification of treatments selected for utilization review;
(g) symptom input means for inputting descriptions of patients' symptoms into said system;
(h) means responsive to input of said patients' symptoms for displaying recommended treatments, for identifying recommended treatments which are selected for utilization review and for displaying indicia identifying said recommended treatments which are selected for utilization review, said means responsive to input of said patients' symptoms being further effective to identify recommended treatments for which ancillary services are indicated;
(i) means responsive to identification of said recommended treatments for identifying payor-approved charges for said treatments;
(j) means for comparing said payor-approved charges for said treatments with corresponding actual charges assessed by a proposed health care provider and for identifying any insufficiency of payor-approved charges compared to said actual charges;
(k) means for supplying said insufficiency by payroll deduction for patients that are paid on organization payrolls;
(l) means including said utilization review means for providing medical care quality control;

(m) means for providing both in-patient and outpatient care; and (n) means including said data bank memory for preparing recommended post-treatment routines.

48. An integrated health care management system according to claim 47 wherein when one of said recommended treatments is selected for utilization review, payment approval is withheld until data is entered into said system confirming completion of said utilization review.

49. An integrated health care management system according to claim 47 wherein said physical profile data include physical examination results.

50. An integrated health care management system according to claim 47 wherein said utilization review means includes second opinion means.

51. An integrated health care management system according to claim 47 wherein said physical profile data include physical examination results and wherein said utilization review means includes second opinion means.

52. A method of managing a comprehensive health care management system utilizing a data processor, data bank memories, input means and payment means comprising:

(a) entering into said data processor data identifying each of a predetermined plurality of persons;

(b) entering into one of said data bank memories an identification of predetermined procedures requiring utilization review;

(c) entering through said input means into said data processor data symbolic of patient symptoms for tentatively identifying a proposed mode of treatment and, when said proposed mode of treatment includes one of said predetermined procedures requiring utilization review, producing indicia indicative thereof; and (d) preventing payment therefor by said payment means until said utilization review has been obtained and data indicative thereof has been entered in said system.

53. A method of managing a health care management system according to claim 52 in which the step of tentatively identifying a proposed mode of treatment further includes checking said proposed mode of treatment and when said proposed mode of treatment includes an ancillary service, producing indicia indicative thereof and providing said ancillary service.

54. A method of managing a health care management system according to claim 52 in which the step of tentatively identifying a proposed mode of treatment further includes the step of tentatively identifying preventive health routines for addressing each of any identified plurality of potentially health-destructive conditions including excessive weight, high blood pressure, smoking, and insufficient exercise.

55. A method of managing a health care management system utilizing a data processor, data bank memories, input means and payment means comprising:

(a) entering into said input means data identifying each of a predetermined plurality of persons;

(b) entering into one of said data bank memories an identification of predetermined items of medical history for said predetermined plurality of persons;

(c) entering into another of said data bank memories an identification of predetermined procedures requiring utilization review; and (d) entering through said input means into said data processor data symbolic of patient symptoms for tentatively identifying a proposed mode of treatment and, when said proposed mode of treatment includes one of said predetermined procedures requiring utilization review, producing indicia indicative thereof; and (e) preventing payment therefor until said utilization review has been obtained and data indicative thereof has been entered in said system.

56. A method of managing a health care management system according to claim 55 in which the step of entering into one of said data bank memories an identification of predetermined items of medical 57. A method of managing a health care management system according claim 55 in which said input means further includes a data input terminal and in which the method further includes the step of entering into said data input terminal of said system said predetermined items of medical history.

58. A method of managing a health care management system according to claim 55 further including the step of storing within said one of said data bank memories information individually relating to each of said predetermined plurality of persons.

59. A method of managing a health care management system according to claim 58 further including the step of verifying authenticity of identifications of said predetermined plurality of persons.

60. A method of managing a health care management system according to claim 59 further including the step of verifying eligibility for treatment of said predetermined plurality of persons.

61. A method of managing a health care management system according to claim 60 wherein the step of verifying the eligibility for treatment of said predetermined plurality of persons further includes the step of identifying pre-selected classes of treatments pre-certified for authorized treatment and payment.

62. A method of managing a health care management system according to claim 57 further including the step of entering data into said data input terminal from a magnetically-encoded medium.

63. A method of managing a health care management system according to claim 57 further including the step of manually entering data input into said data terminal through a manual keyboard.

64. A method of managing a health care management system according to claim 55 further including the step of accessing one of said data bank memories to identify symptoms for diagnosis of each of a predetermined plurality of illnesses.

65. A method of managing a health care management system according to claim 55 further including the step of accessing said data symbolic of patient symptoms and identifying a proposed mode of treatment for each of a predetermined plurality of illnesses.

66. A method of managing a health care management system according to claim 64 further including the step of accessing said data symbolic of patient symptoms and identifying a proposed mode of treatment for each of a predetermined plurality of illnesses.

67. A method of managing a comprehensive health care management system comprising:

(a) providing a data input terminal for said system for entering into said system data identifying each of a predetermined plurality of persons;

(b) establishing a data bank memory operatively connected to said system for including an identification of predetermined procedures requiring second options;

(c) entering in said data input terminal data symbolic of patient symptoms;

(d) establishing payment means;

(e) accessing said data symbolic of patient symptoms for tentatively identifying a proposed mode of treatment and, (f) when said proposed mode of treatment includes one of said predetermined procedures requiring a second opinion, producing indicia indicative thereof and preventing payment therefor by said payment means until a second opinion has been obtained.

68. A method of managing a health care management system according to claim 67 wherein when said proposed mode of treatment includes an ancillary service, the additional step of producing indicia indicative thereof and for providing said ancillary service.

69. A method of managing a health care management system according to claim 67 further including the step of tentatively identifying preventive health routines for addressing each of any identified plurality of potentially health-destructive conditions including excessive weight, high blood pressure, smoking, and insufficient exercises.

70. A method of managing a comprehensive health care management system utilizing a data processor, data bank memories, input means and payment means comprising:

(a) providing a data input terminal for entering into said system data identifying each of a predetermined plurality of persons;

(b) establishing a first system data bank memory and entering into said first data bank memory predetermined items of medical history for said predetermined plurality of persons;

(c) establishing another system data bank memory and entering into said another data bank memory information including an identification of predetermined procedures requiring second opinions;

(d) entering into said data processor information symbolic of patient symptoms;

(e) establishing payment means;

(f) accessing one of said data bank memories for tentatively identifying a proposed mode of treatment; and, (g) when said proposed mode of treatment includes one of said predetermined procedures requiring a second opinion, for producing indicia indicative thereof and for preventing payment therefor by said payment means until a second opinion has been obtained.

71. A method of managing a health care management system according to claim 70 in which the step of entering into said first system data bank memory predetermined items of medical history includes step of including physical profiles of said predetermined plurality of persons.

72. A method of managing a health care management system according to claim 70 further including the step of accessing said predetermined items of medical history.

73. A method of managing a health care management system according to claim 70 wherein the step of entering into said first system data bank memory predetermined items of medical history further includes the step of entering into one of said data banks data designating the identity of the payor for health care for each of said predetermined plurality of persons.

74. A method of managing a health care management system according to claim 73 further including means for verifying the authenticity of identifications of said predetermined plurality of persons.

75. A method of managing a health care management system according to claim 74 further including the step of verifying eligibility for treatment of said predetermined plurality of persons.

76. A method of managing a health care management system according to claim 75 further including the step of verifying the eligibility for treatment of said predetermined plurality of persons and identifying preselected classes of treatments pre-certified for authorized treatment and payment.

77. A method of managing a health care management system according to claim 72 further including the step of entering data into said system from a magnetically-encoded medium.

78. A method of managing a health care management system according to claim 72 further including the step of entering data into said system from a manual keyboard.

79. A method of managing a health care management system according to claim 70 further including the step of accessing one of said data bank memories to identify symptoms for diagnosis of each of a predetermined plurality of illnesses.

80. A method of managing a health care management system according to claim 70 further including the step of entering into one of said data bank memories data representing treatment for each of a predetermined plurality of illnesses.

81. A method of managing a health care management system according to claim 79 further including the step of entering into one of said data bank memories data representing treatment for each of a predetermined plurality of illnesses.

82. A method of managing a health care management system having a data processor comprising:

(a) providing a data input terminal for entering data identifying each of a predetermined plurality of persons being on a payroll of an organization;

(b) providing a data bank memory containing predetermined items of medical history for said predetermined plurality of persons;

(c) providing another data bank memory including an identification of predetermined medical procedures and pre-approved levels of payments for said predetermined medical procedures;

(d) entering into said system data indicative of performance of one of said predetermined medical procedures; and (e) examining a level of charge made by a provider of medical services for the performed procedure and, if said level of charge exceeds the pre-approved level of payment for said procedure, for causing payment of the exceeded amount by payroll deduction.

83. A method of managing a health care management system having a data processor comprising:

(a) providing a first data input terminal at the location of a medical services provider;

(b) entering into said system through said first data input terminal data identifying each of a predetermined plurality of persons being on a payroll of an organization;

(c) providing a second data terminal at the location of said organization;

(d) providing a data bank memory containing predetermined items of medical history for said predetermined plurality of persons;

(e) providing another data bank memory including an identification of predetermined medical procedures and pre-approved levels of payments for said predetermined medical procedures; and (f) entering into said system data indicative of performance of one of said predetermined medical procedures;

(g) examining a level of charge made by a provider of medical services for the performed procedure and, if said level of charge exceeds the pre-approved level of payment for producing at the location of said second data terminal indicia indicative thereof and for permitting authorization for excess payment by said organization.

84. A method of managing a health care management system comprising:

(a) providing a data input terminal;

(b) entering into said system through said data input terminal data identifying each of a predetermined plurality of persons being subject to workmen's compensation;

(c) providing in said system a data bank memory;

(d) entering into said system an identification of predetermined medical procedures and pre-approved levels of workmen's compensation payments for said predetermined medical procedures; and (e) examining a level of charge made by a provider of medical services for a predetermined procedure performed on one of said predetermined plurality of persons and, if said level of charge exceeds said pre-approved level of payment for said procedure, for identifying the exceeded amount and for permitting the payment of the exceeded amount by said one of said predetermined plurality of persons.

85. A method of managing a health care management system comprising:

(a) providing a data input terminal;

(b) entering data into said system for identifying each of a predetermined plurality of persons;

(c) providing a data bank memory containing predetermined items of medical history for each of said predetermined plurality of persons;

(d) providing in said data bank memory an identification of predetermined procedures requiring ancillary services; and (e) tentatively identifying a proposed mode of treatment and, when said proposed mode of treatment includes one of said ancillary services, for producing indicia indicative thereof and for providing said one of said ancillary services.

86. A method of managing a health care management system according to claim 85 in which said predetermined items of medical history include physical profiles of said predetermined plurality of persons.

87. A method of managing a health care management system according to claim 85 in which said system further includes the step of entering into said system said predetermined items of medical history through said data input terminal.

88. A method of managing a health care management system according to claim 87 further including the step of verifying authenticity of identifications of said predetermined plurality of persons.

89. A method of managing a health care management system according to claim 88 further including the step of verifying eligibility for treatment of said predetermined plurality of persons.

90. A method of managing a health care management system according to claim 89 further including the step of identifying pre-selected classes of treatments pre-certification for authorized treatment and payment.

91. A method of managing a health care management system according to claim 85 further including the step of tentatively identifying preventive health routines for addressing each of a plurality of potentially health-destructive conditions including excessive weight, high blood pressure, smoking, insufficient and exercise.

92. A method of managing a health care management system according to claim 87 further including the step of entering data into said system from a magnetically-encoded medium.

93. A method of managing a health care management system according to claim 87 further including the step of entering data into said system through a manual keyboard.

94. A method of managing a health care management system according to claim 85 including the step of entering into said data bank memory an identification of symptoms for diagnosis of each of a predetermined plurality of illnesses.

95. A method of managing a health care management system according to claim 85 further including the step of entering into said data bank memory data representing treatment for each of a predetermined plurality of illnesses.

96. A method of managing a health care management system according to claim 94 further including the step of introducing into said data bank memory data representing treatment for each of said predetermined plurality of illnesses.

97. A method of managing a health care management system comprising:

(a) providing a data input terminal for entering data identifying each of a predetermined plurality of persons;

(b) providing a data bank memory containing predetermined items of medical history including physical profile data for said predetermined plurality of persons;

(c) including in said data bank memory health regimen recommendation data for each of a predetermined plurality of physical profiles;

(d) generating individualized preventive health regimen recommendations for each of said predetermined plurality of persons including diet and exercise;

(e) recording in said data bank memory symptoms associated with each of a predetermined plurality of health problems;

(f) recording in said data bank memory recommended treatment protocols for each of said predetermined plurality of health problems;

(g) selecting treatments for utilization review;

(h) inputting into said system data representing patients' symptoms;

(i) accessing said data bank memory means responsive to input of said patients' symptoms for displaying recommended treatments, for identifying recommended treatments which are selected for utilization review, for displaying indicia identifying said treatments which are selected for utilization review, and identifying those recommended treatments for which ancillary services are indicated;

(j) identifying payor-approved charges for said treatments;

(k) comparing said payor-approved charges for said treatments with corresponding actual charges assessed by a proposed health care provider and identifying any insufficiency of payor-approved charges compared to said actual charges;

(l) providing payroll deduction and supplying said insufficiency by payroll deduction for patients that are paid on organization payrolls;

(m) providing medical care quality control;

(n) providing both in-patient and out-patient care; and (o) preparing recommended post-treatment routines.

98. A method of managing an integrated health care management system according to claim 97 further including the step of withholding payment approval for one of said treatments selected for utilization review, until data is entered into said system confirming completion of said utilization review.

99. A method of managing an integrated health care management system according to claim 97 further including the step of storing in said data bank memory physical examination results.

100. A method of managing an integrated health care management system according to claim 97 further including the step of identifying selected procedures for second opinions and wherein said utilization review includes providing second opinions.

101. A method of managing an integrated health care management system according to claim 97 further including the steps of storing examination results in said data bank memory and identifying selected procedures for second opinions.

102. A method of managing an integrated health care management system having input means, payment means and memory storage comprising:

(a) storing through said input means into said memory storage personal health profile data for each of a predetermined plurality of persons;

(b) storing into said memory storage symptoms and treatment data for each of a predetermined plurality of health profiles and problems;

(c) storing in said memory storage criteria for identifying treatments requiring utilization review;

(d) storing in said memory storage criteria for identifying treatments requiring second opinions;

(e) entering into said system information identifying a proposed medical treatment for one of said plurality of persons;

(f) identifying whether or not said proposed medical treatment requires utilization review; and (g) preventing said system from approving payment for said proposed medical treatment if said proposed medical treatment requires utilization review until such utilization review has been conducted.

* * * * *